US008202551B2

United States Patent
Li et al.

(10) Patent No.: US 8,202,551 B2
(45) Date of Patent: Jun. 19, 2012

(54) TISSUE ENGINEERED CARTILAGE, METHOD OF MAKING SAME, THERAPEUTIC AND COSMETIC SURGICAL APPLICATIONS USING SAME

(75) Inventors: Wan-Ju Li, Madison, WI (US); Rocky S. Tuan, Bethesda, MD (US)

(73) Assignee: The United States of America, as represented by the Secretary, Department of Health & Human Services, Washington, DC (US)

( * ) Notice: Subject to any disclaimer, the term of this patent is extended or adjusted under 35 U.S.C. 154(b) by 725 days.

(21) Appl. No.: 11/922,251

(22) PCT Filed: Jun. 15, 2006

(86) PCT No.: PCT/US2006/023477
§ 371 (c)(1),
(2), (4) Date: Apr. 23, 2009

(87) PCT Pub. No.: WO2006/138552
PCT Pub. Date: Dec. 28, 2006

(65) Prior Publication Data
US 2010/0061962 A1    Mar. 11, 2010

Related U.S. Application Data

(60) Provisional application No. 60/690,988, filed on Jun. 15, 2005.

(51) Int. Cl.
*A01N 65/00* (2009.01)
(52) U.S. Cl. ..................................................... 424/725
(58) Field of Classification Search ........................ None
See application file for complete search history.

(56) References Cited

OTHER PUBLICATIONS

W. Li et al., "Biological response of chondrocytes cultured in three-dimensional nanofibrous poly(ε-caprolactone) scaffolds", *Journal of Biomedical Materials Research. Part A*, 67(4), pp. 1105-1114 (Dec. 15, 2003).
R. Vasita, "Nanofibers and their applications in tissue engineering", *International Journal of Nanomedicine*, 1(1), pp. 15-30 (2006).
W. Li et al., "Electrospun nanofibrous structure: A novel scaffold for tissue engineering", *Journal of Biomedical Materials Rsearch*, 60(4), pp. 613-621 (Jun. 15, 2002).
W. Li et al., "A three-dimensional nanofibrous scaffold for cartilage tissue engineering using human mesenchymal stem cells", *Biomaterials, Elsevier Science Publishers*, 26(6), pp. 599-609 (Jan. 1, 2005).

*Primary Examiner* — Michael Meller
(74) *Attorney, Agent, or Firm* — Edwards Wildman Palmer LLP; Peter F. Corless; Andrew W. Shyjan

(57) ABSTRACT

Cartilage has been constructed using biodegradable electrospun polymeric scaffolds seeded with chondrocytes or adult mesenchymal stem cells. More particularly engineered cartilage has been prepared where the cartilage has a biodegradable and biocompatible nanofibrous polymer support prepared by electrospinning and a plurality of chondocytes or mesenchymal stem cells dispersed in the pores of the support. The tissue engineered cartilages of the invention possess compressive strength properties similar to natural cartilage. Methods of preparing engineered tissues, including tissue engineered cartilages, are provided in which an electrospun nanofibrous polymer support is provided, the support is treated with a cell solution and the polymer-cell mixture cultured in a rotating bioreactor to generate the cartilage. The invention provides for the use of the tissue engineered cartilages in the treatment of cartilage degenerative diseases, reconstructive surgery, and cosmetic surgery.

5 Claims, 13 Drawing Sheets

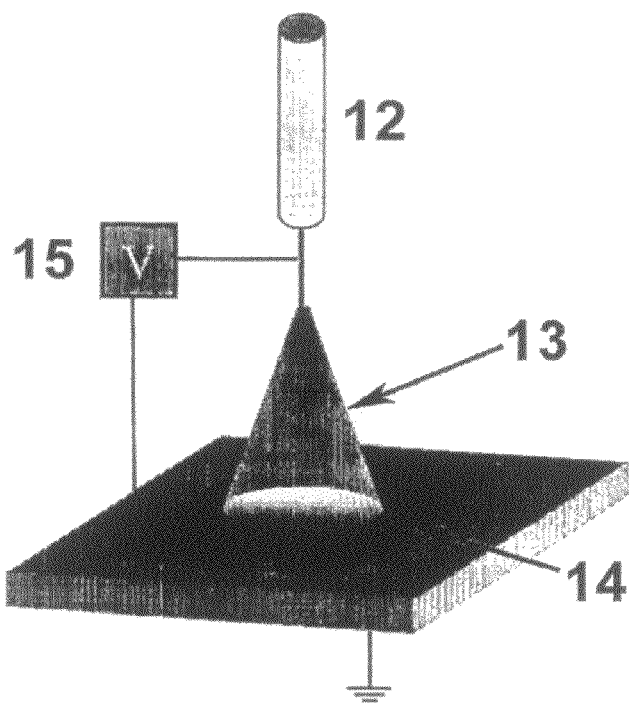
FIG 1
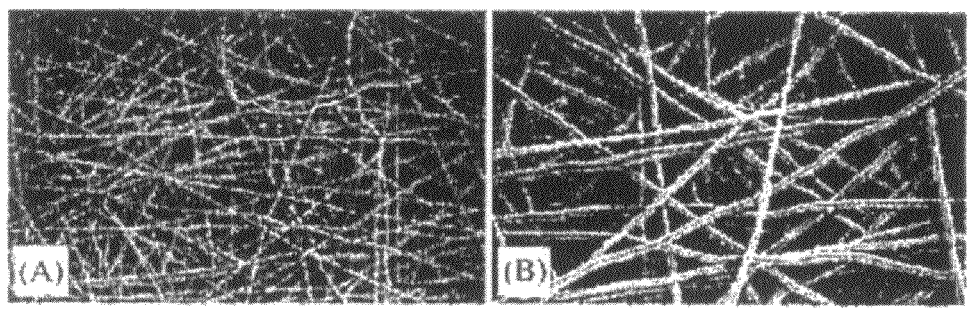
Fig. 2. Bar: A = 30 μm, B = 10 μm.

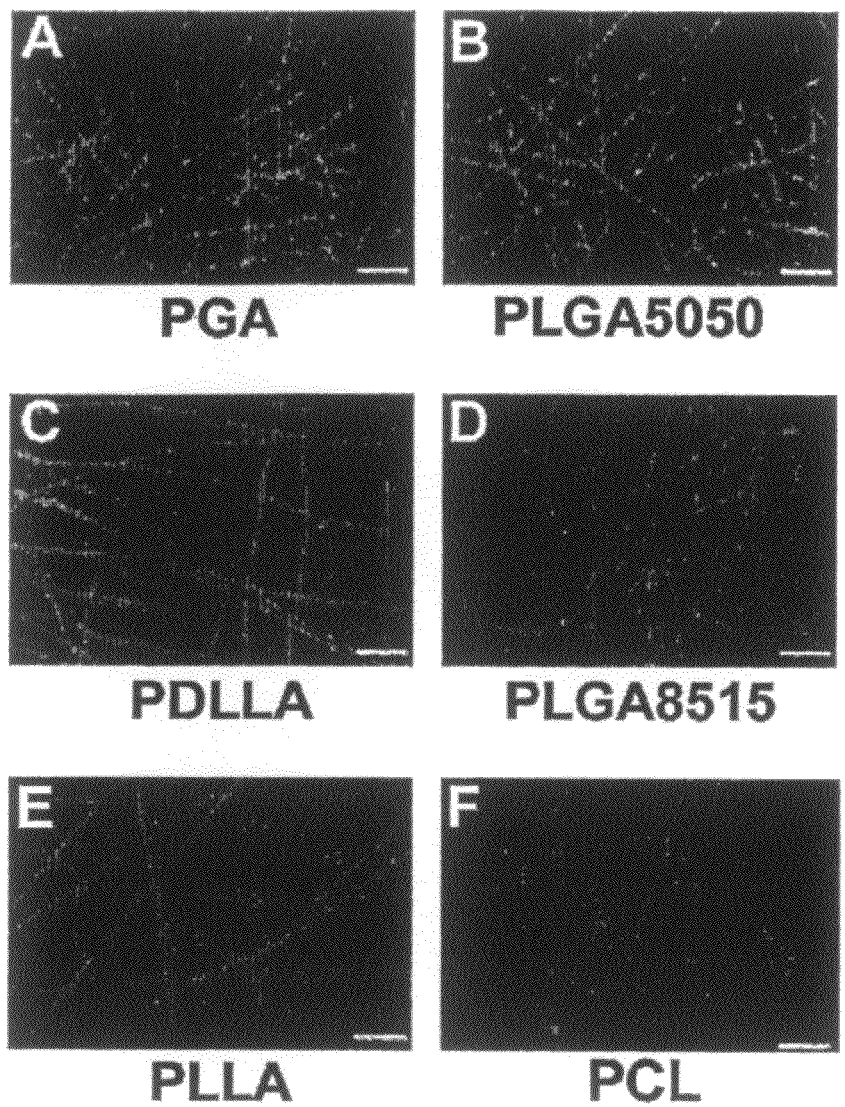
FIG 3A-F Scale 10 μm

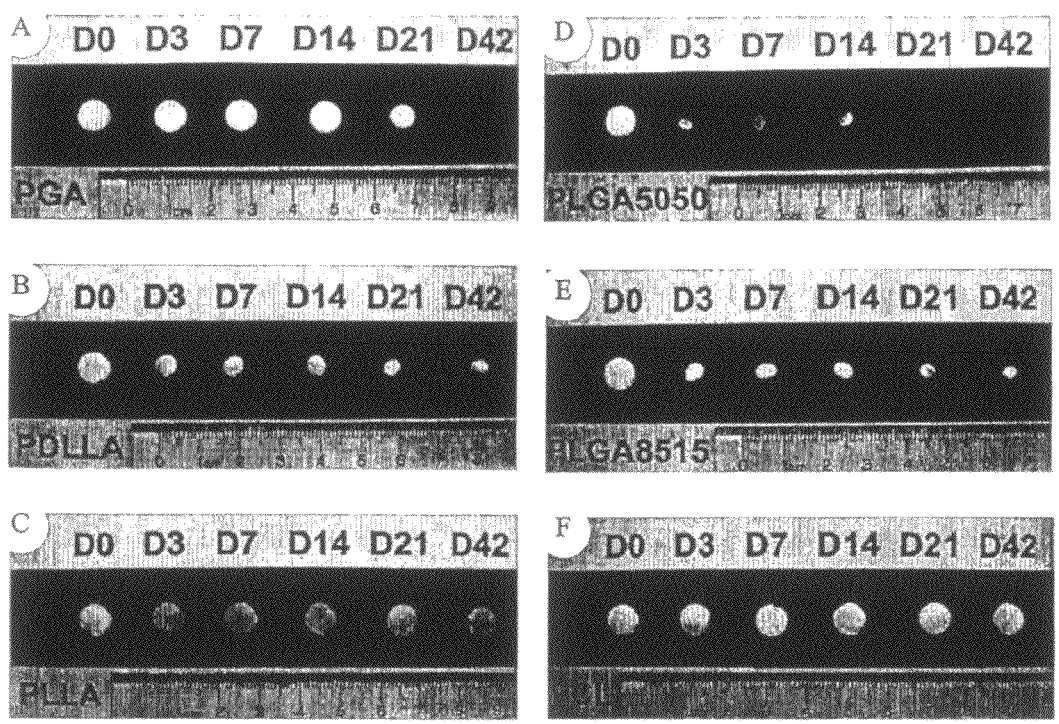
FIG 4A-F

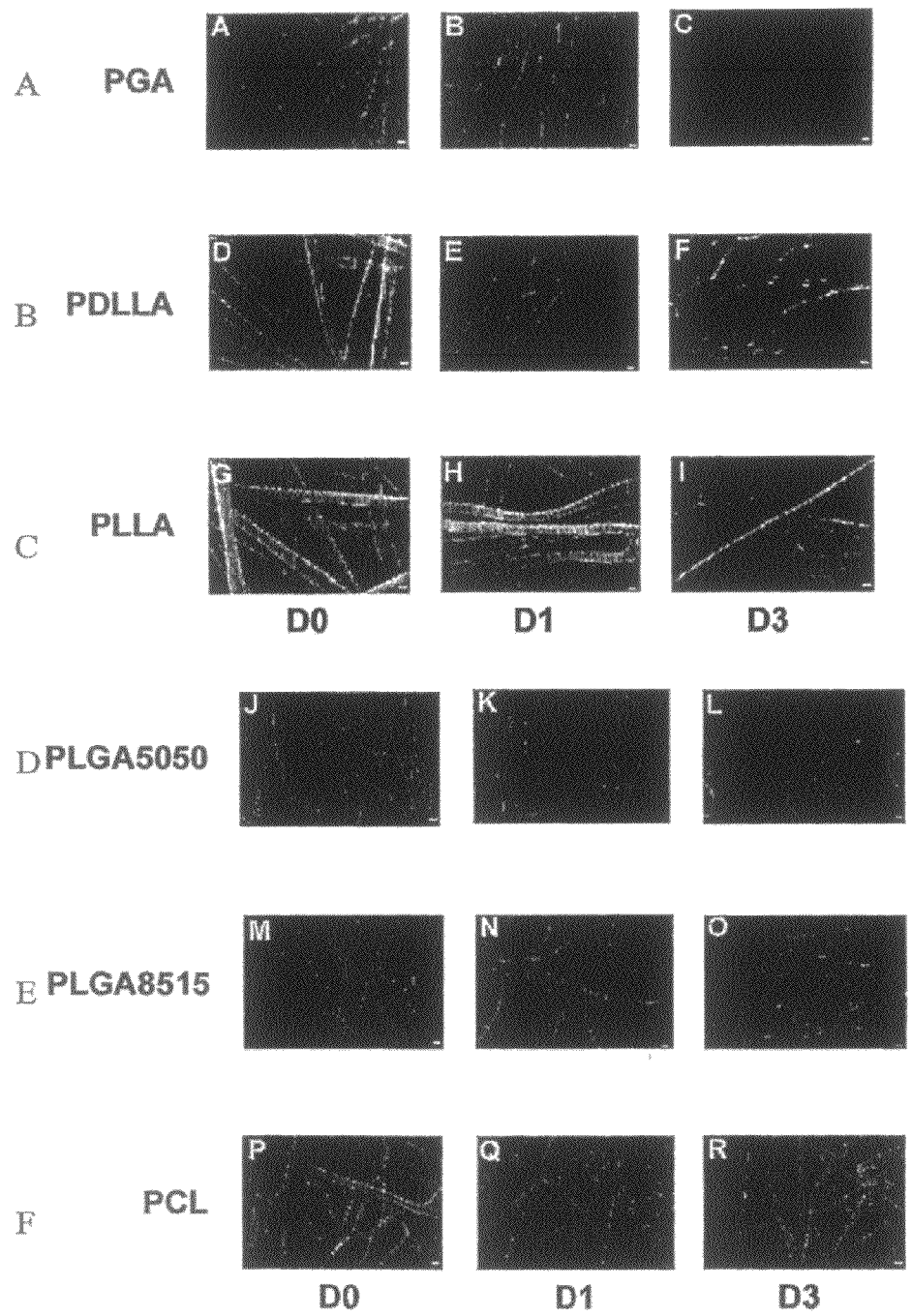
FIG 5A-F

TISSUE ENGINEERED CARTILAGE, METHOD OF MAKING SAME, THERAPEUTIC AND COSMETIC SURGICAL APPLICATIONS USING SAME

The present application claims the benefit of U.S. provisional application No. 60/690,988, filed Jun. 15, 2005, which is incorporated herein by reference in its entirety.

STATEMENT REGARDING FEDERALLY SPONSORED RESEARCH OR DEVELOPMENT

Research supporting this application was carried out by the United States of America as represented by the Secretary, Department of Health and Human Services.

FIELD OF INVENTION

The present invention relates to tissue engineered cartilage comprising a nanofibrous biocompatible polymer support having chondocytes dispersed therein, which has compressive strength equal to natural cartilage, methods of fabricating tissue engineered cartilage by culturing a mixture of stem cells or chondocytes and a electrospun nanofibrous polymer substrate in a suitable bioreactor and methods of treatment comprising implantation of tissue engineered cartilage into a patient.

BACKGROUND OF THE INVENTION

Diseased or damaged cartilage has often been replaced by an artificial material, cadaver tissue, or donated, allogenic tissue. Tissue engineering offers an attractive alternative whereby a live, natural tissue is generated from a construct made up of a patient's own cells in combination with a biodegradable scaffold for replacement of defective tissue.

Cartilage defects resulting from aging, joint injury, and developmental disorders cause joint pain and loss of mobility. It would be desirable to provide a tissue engineering approach provides a cell-based therapy to repair articular cartilage defects and to restore joint functions. In prior attempts to tissue engineer cartilage, chondrocytes and mesenchymal stem cells (MSCs) have been used for cartilage regeneration, and the choice of cell type determines the strategy of cartilage tissue engineering in vitro.

Existing engineered cartilage and the methods of making same generate materials which do not possess the mechanical properties of natural cartilage. Thus, cartilage generated by seeding a hydrogel or preformed three dimensional polymeric scaffold are less resistant to compressive force than natural cartilage. Conventional methods of making cartilage, e.g., using a hydrogel or preformed three dimensional polymeric scaffold, result in despecification of the seeded chondocytes, poor intercellular contact between chondocytes, and/or insufficient mechanical strength.

The electrospinning process is a simple, economical means to produce supports or scaffolds of ultra-fine fibers derived from a variety of biodegradable polymers (Li W J, et al. J Biomed Mater Res 2002;60:613-21). Nanofibrous scaffolds (NFSs) formed by electrospinning, by virtue of structural similarity to natural extracellular matrix (ECM), may represent promising structures for tissue engineering applications. We have previously shown that electrospun three-dimensional NFSs are characterized by high porosity with a wide distribution of pore diameter, high-surface area to volume ratio, and morphological similarities to natural collagen fibrils (Li W J, et al., J Biomed Mater Res 2002;60:613-21). These physical characteristics promote favorable biological responses of seeded cells in vitro, including enhanced cell attachment, proliferation, and maintenance of the chondrocytic phenotype (Li W J, et al., J Biomed Mater Res 2002;60: 613-21; and Li W J, et al. J Biomed Mater Res 2003;67A: 1105-14).

It would be desirable to provide tissue engineered cartilage materials and methods of making same which are suitable for preparing cartilage suitable for use in repairing cartilage defects associated with degenerative joint diseases or in plastic/cosmetic surgery requiring repair or augmentation of cartilaginous tissue. More particularly, it would be desirable to provide methods of making high strength cartilage, tissue engineered cartilage prepared thereby and methods of treatment using such high strength tissue engineered cartilage.

SUMMARY OF THE INVENTION

Described herein are engineered tissues, particularly tissue engineered cartilage, methods of generating the engineered tissue cartilage or other tissues, and methods of using the tissue engineered cartilage or other tissues in various applications utilizing engineered tissues, including for example, therapeutic or prophylactic replacement or supplementation of cartilage.

One aspect is a tissue engineered cartilage having a peak compressive stress (Young's modulus) of greater than 250 MPa, which tissue engineered cartilage is composed of a plurality of chondocytes dispersed in a nanofibrous polymer support comprising a plurality of polymer nanofibers. In other aspects, the each of the plurality of chondocytes is in contact with at least one, at least two, or at a plurality of other chondocytes dispersed in the polymer support. In certain tissue engineered cartilages provided herein possess a peak compressive strength of at least about 300 MPa, about 400 MPa or about 500 MPa or a compressive strength of between about 250-1000 MPa, between about 300-1000 MPa, between about 300-900 MPa, between about 400-900 Mpa, or between about 600-900 MPa.

In other aspects, the nanofibrous polymer support of the tissue engineered cartilage is composed of at least one biodegradable and biocompatible polymer which can be processed by electrospinning to form sub-micron fibers. Yet other aspects, the nanofibrous polymer support comprises polymer nanofibers having a diameter of less than 1 micron or having a diameter of between 10 nm to 1 micron, 50 nm to 1 micron, 100 nm to 1 micron, or 200 nm to 700 nm.

In other aspects, the nanofibrous polymer supports comprise electrospun polyester polymers which have been approved for use in surgical applications by the FDA or equivalent regulatory agency. In general, electrospinning is a process of producing nanofibers or microfibers of a polymer in which a high voltage electric field is applied to a solution of the polymer. The drawn nanofibers are collected in on a target covering one of the electrodes. By careful regulation of inter-electrode distance, voltage, solvent, and polymer solution viscosity the diameter of the resultant electrospun fibers can be controlled. Optimization of the elecrospinning process results in formation of polymer nanofibers have a substantially uniform diameter. In certain aspects, a two dimensional static target is used in the electrospinning process to generate a randomly oriented non-woven mat of fibers deposited onto the target.

Another aspect is a method of preparing tissue engineered cartilage comprising (a) preparing a nanofibrous biocompatible polymer support;

(b) contacting a suspension of cells with the surface of the support provided in (a) to form a polymer matrix having cells dispersed therein;

(c) culturing the cell-polymer matrix in a bioreactor with a culture medium under conditions conducive to growth of chondocytes into a tissue engineered cartilage.

Yet another aspect is a method of preparing tissue engineered cartilage comprising (a) preparing an expanded nanofibrous biocompatible polymer support;

(b) contacting a suspension of cells with the support provided in (a) to form a polymer matrix having cells dispersed therein;

(c) compressing the cell-polymer matrix prepared in (b) to create cell-cell contact and cell-polymer contact;

(d) culturing the compressed cell-polymer matrix prepared in (c) in a bioreactor with a culture medium under conditions conducive to growth of chondocytes into a tissue engineered cartilage having a peak compressive stress (Young's modulus) of greater than 250 MPa.

Another aspect is a method of forming cartilage in vivo, the method comprising the steps of (a) providing a nanofibrous polymer support comprising a plurality of polymer nanofibers; and (b) inserting the nanofibrous polymer support into a patient at the position suitable for formation of new cartilage.

In other aspects, the invention provides methods of repairing, replacing and/or augmenting cartilage in a patient for treatment or prevention of diseases or disorders or for cosmetic purposes. In certain aspects, a method of treating cartilage damage is provided in which the method comprising the steps of:

(a) providing a tissue engineered cartilage having a peak compressive stress (Young's modulus) of greater than 250 MPa, which tissue engineered cartilage is composed of a plurality of chondocytes dispersed in a nanofibrous polymer support comprising a plurality of polymer nanofibers or a tissue engineered cartilage prepared by the methods provided herein;

(b) inserting the tissue engineered cartilage into a patient at the location of damaged cartilage.

Another aspect is a method for treating cartilage damage, the method comprising the steps of (a) harvesting chondocytes or MSC cells from the patient (b) preparing tissue engineered cartilage by one of the methods provided herein, wherein the cells are the chondocytes or MSC cells harvested from the patient;

(c) implanting the tissue engineered cartilage in the patient in the locus having damaged cartilage.

Yet another aspect is a method for cosmetic or reconstructive surgery, the method comprising the steps of (a) providing a tissue engineered cartilage having a peak compressive stress (Young's modulus) of greater than 250 MPa, which tissue engineered cartilage is composed of a plurality of chondocytes dispersed in a nanofibrous polymer support comprising a plurality of polymer nanofibers or a tissue engineered cartilage prepared by the methods provided herein;

(b) inserting the tissue engineered cartilage into a patient.

In another aspect, the invention provides a method for cosmetic or reconstructive surgery, the method comprising the steps of (a) harvesting chondocytes or MSC cells from the patient;

(b) preparing tissue engineered cartilage by a method provided herein, wherein the cells are the chondocytes or MSC cells harvested from the patient;

(c) implanting the tissue engineered cartilage in the patient.

Yet another aspect is a methods of preparing a tissue engineered tissue comprising the steps of (a) preparing a nanofibrous biocompatible polymer support;

(b) contacting a suspension of cells with the surface of the support to form a polymer matrix having cells dispersed therein;

(c) culturing the cell-polymer matrix in a bioreactor with a culture medium under conditions conducive cell growth and differentiation to tissue engineered tissue.

Still another aspect is a method of preparing a tissue engineered tissue comprising the steps of (a) preparing an expanded nanofibrous biocompatible polymer support;

(b) contacting a suspension of cells with the support to form a polymer matrix having cells dispersed therein;

(c) compressing the cell-polymer matrix to create cell-cell contact and cell-polymer contact;

(d) culturing the compressed cell-polymer matrix in a bioreactor with a culture medium under conditions conducive cell growth and differentiation to tissue engineered tissue.

Other aspects and embodiments of the invention are discussed below.

BRIEF DESCRIPTION OF THE DRAWING

For a fuller understanding of the nature and desired objects of the present invention, reference is made to the following detailed description taken in conjunction with the accompanying drawing figures wherein like reference character denote corresponding parts throughout the several views and wherein:

FIG. 1 is a schematic of electrospinning apparatus (10) for the preparation of nanofibrous polymer supports suitable for use in the invention;

FIG. 2. is a scanning electron microscope image of an electrospun PCL-based nanofibrous scaffold at (A) low and (B) high magnification. The scaffold contains randomly oriented uniformly sized fibers of an average diameter of 700 nm (black legend is 30 μm in FIG. 2A and 10 μm in FIG. 2B);

FIG. 3A-F provides a series of microscopic images of various nanofibrous scaffolds which are contemplated for use in the methods and cartilage provided herein (PGA is poly (glycolic acid), PDLLA is poly(D,L-lactic acid), PLLA is poly(L-lactic acid), PLGA5050 is poly(D,L-lactide-co-glycolide 50:50), PLGA8515 is poly(D,L-lactide-co-glycolide 85:15), and PCL is poly(epsilon-caprolactone));

FIG. 4A-F provides a macroscopic observation of nanofibrous scaffolds exposed to a phosphate buffered solution at days 3, 7, 14, 21, and 42 (PGA is poly(glycolic acid), PDLLA is poly(D,L-lactic acid), PLLA is poly(L-lactic acid), PLGA5050 is poly(D,L-lactide-co-glycolide 50:50), PLGA8515 is poly(D,L-lactide-co-glycolide 85:15), and PCL is poly(epsilon-caprolactone));

FIG. 5A-F is a series of scanning electron microscope images of nanofibrous non-woven mats composed of PGA, PDLLA, PLLA, PLGA5050, PLGA8515, and PCL. Images are provided prior to exposure to a degradation medium (D0), after one day in the degradation medium (D1) and after three days in the degradation medium (D3). In the figure, PGA is poly(glycolic acid), PDLLA is poly(D,L-lactic acid), PLLA is poly(L-lactic acid), PLGA5050 is poly(D,L lactide-co-glycolide 50:50), PLGA8515 is poly(D,L-lactide-co-glycolide 85:15), and PCL is poly(epsilon-caprolactone);

DESCRIPTION OF THE PREFERRED EMBODIMENT(S)

Figure 6:
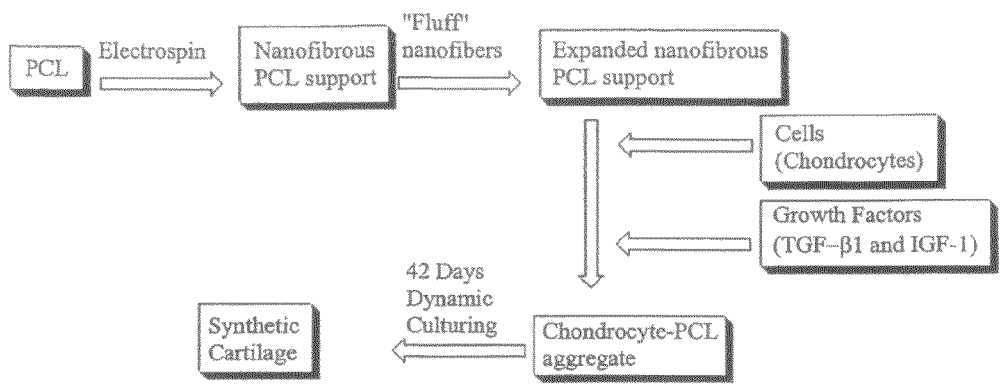
FIG. 6 is a tissue engineered flow chart of one of the methods of preparing tissue engineered cartilage provided herein and exemplified in Example 4.

Although a preferred embodiment of the invention has been described using specific terms, such description is for illustrative purposes only, and it is to be understood that changes and variations may be made without departing from the spirit or scope of the following claims.

Methods and materials to form tissues, especially cartilage, are described wherein cells, e.g., chondrocytes or mesenchymal stem cells, are seeded onto or into a biocompatible, biodegradable, nanofibrous polymer scaffold which cell-polymer matrix is then cultured in a rotating bioreactor to form the tissue or cartilage. The product tissue or cartilage generated in the methods of the invention is implantation into a patient in therapeutic, prophylactic or cosmetic procedures.

In certain aspects, a method of preparing tissue engineered cartilage is provided in which the method comprises the steps of (a) preparing a nanofibrous biocompatible polymer support;

(b) contacting a suspension of cells with the surface of the support provided in (a) to form a polymer matrix having cells dispersed therein;

(c) culturing the cell-polymer matrix in a bioreactor with a culture medium under conditions conducive to growth of chondocytes into a tissue engineered cartilage.

Yet another aspect is a method of preparing tissue engineered cartilage comprising the steps of:

(a) preparing an expanded nanofibrous biocompatible polymer support;

(b) contacting a suspension of cells with the support provided in (a) to form a polymer matrix having cells dispersed therein;

(c) compressing the cell-polymer matrix prepared in (b) to create cell-cell contact and cell-polymer contact;

(d) culturing the compressed cell-polymer matrix prepared in (c) in a bioreactor with a culture medium under conditions conducive to growth of chondocytes into a tissue engineered cartilage having a peak compressive stress (Young's modulus) of greater than 250 MPa.

Nanofibrous Polymer Scaffolds

The nanofibrous polymer scaffold can be manufactured by any method capable of generating a random web of nanofibers. Preferred nanofibrous polymer scaffold are composed of one or more biodegradable and/or biocompatible polymer. In certain aspects, the nanofibrous polymer scaffold is manufactured from a biodegradable polymer which is dimensionally stable for the duration of the tissue engineering process. In certain aspects, nanofibrous polymer scaffolds comprise nanofibers having a thickness of less than about 1 μm, less than about 750 nm, or a thickness of between about 50 nm and about 800 nm. In certain other aspects, the nanofibrous polymer scaffold comprises nanofibers having a thickness of between about 100 nm and about 700 nm or between about 200 nm and about 600 nm. Typically preferred nanofibrous polymer scaffolds comprise a random web of nanofibers which have an interfiber distance and nanofiber thickness which approximates the parameters present in the collagen matrix of natural cartilage.

In other aspects, the nanofibrous polymer supports comprise electrospun nanofibers. Nanofibers prepared by electrospinning provide a nanofibrous polymer support possessing a high surface area to volume ratio and improved mechanical properties relative to hydrogels and other polymeric supports. Although not wishing to be bound by theory, certain nanofibrous polymer supports prepared by electrospinning mimic the fiber diameter and interfiber characteristics of collagen and the extracellular matrix of healthy cartilage.

In general, electrospinning is a process of producing nanofibers or microfibers of a polymer in which a high voltage electric field is applied to a solution of the polymer. The drawn nanofibers are collected in on a target covering one of the electrodes. By careful regulation of inter-electrode distance, voltage, solvent, and polymer solution viscosity the diameter of the resultant electrospun fibers can be controlled. Optimization of the elecrospinning process results in formation of polymer nanofibers have a substantially uniform diameter.

The term "nanofibrous polymer support" is intended to refer to materials composed of a plurality of polymeric nanofibers. FIG. 1 is a schematic diagram of an electrospinning apparatus (10), which consists of a glass syringe containing polymer solution (12), nanofiber jet (13), copper collecting plate (14), which optionally has a removable collection layer disposed thereon (not shown), and power supply (15). In certain embodiments, the nanofibrous polymer support comprises nanofibers composed of at least one polymer. That is, the nanofibrous polymer support is composed of nanofibers composed of a polymer, copolymer, or a blend of polymers or the nanofibrous polymer support comprises two or more compositionally distinct polymeric nanofibers. In certain embodiments, the nanofibrous polymer support is composed of a plurality of uniform thickness nanofibers prepared by an electrospinning process using a solution of one or more biocompatible, bioabsorbable or biodegradable polymers.

In other aspects, the nanofibrous polymer support of the tissue engineered cartilage is composed of at least one biodegradable and biocompatible polymer which can be processed by electrospinning to form sub-micron fibers. In certain aspects, the nanofibrous polymer support is composed of one or more biodegradable biocompatible polyesters. In certain embodiments the biodegradable polyester is a polymer comprising one or more monomers selected from glycolic acid, lactic acid, epsilon-lactone, glycolide, or lactide. By "comprises a monomer" is intended a polymer which is produced by polymerization of the specified monomer, optionally in the presence of additional monomers, which can be incorporated into the polymer main chain. The FDA has approved poly((L)-lactic acid), poly((L)-lactide), poly(epsilon-caprolactone) and blends thereof for use in surgical applications, including medical sutures. An advantage of these tissue engineered absorbable materials is their degradability by simple hydrolysis of the ester linkage in the polymer main chain in aqueous environments, such as body fluids. The degradation products are ultimately metabolized to carbon dioxide and water or can be excreted from the body via the kidney.

In yet other aspects, the nanofibrous polymer scaffold is composed of bioabsorbable materials selected from biopolymers including collagen, gelatin, alginic acid, chitin, chitosan, fibrin, hyaluronic acid, dextran, polyamino acids, polylysine, and copolymers of these materials. Any combination, copolymer, polymer or blend thereof of the above examples is contemplated for use according to the present invention. Such bioabsorbable materials may be prepared by known methods.

In certain aspects, the nanofibrous polymer support comprises nanofibers composed of a biocompatible, biodegradable and/or bioabsorbable material and at least one bioactive molecule. Proteins, non-peptidic therapeutic agents and DNA are generally preferred bioactive molecules for inclusion in the nanofibers of the nanofibrous polymer support. In certain applications proteins, such as growth factors, cytokines, and other therapeutic protein-based drugs, non-protein-based drugs, and DNA, can be incorporated into the biodegradable nanofibers for the programming release to enhance cartilage growth. In certain applications, the bioactive molecules incorporated into the nanofibrous polymer support continuously supplements growth factors such as TGF-beta1 by release of the bioactive molecule from the support by degradation or absorption of the polymer or leaching of the bioactive molecule from the support. In certain applications where the nanofibrous polymer support is composed of a biodegradable polymer having a growth factor dispersed therein, the growth factor is released from the polymer during the degradation process to the surrounding cells endogenously both in vitro and in vivo. The slow release of the bioactive molecule may beneficially deliver additional growth factors to engineered tissue incorporated in vivo in a patient. In certain other applications, incorporating DNA into the nanofibers of the nanofibrous polymer support can genetically instruct (transfect or transduce) cells for favorable cell activities.

In certain other aspects, the nanofibrous polymer support comprises nanofibers coated with one or more bioactive molecules. In certain aspects, electrospun nanofibers can be coated with bioactive proteins, other peptide sequences, bioactive molecules and/or DNA to enhance cell adhesion, migration, proliferation and differentiation. Certain suitable proteins include but are not limited to fibronectin, vitronectin, collagens, laminin and the like. Certain other peptide sequences include but are not limited to RGD (arginine-glycine-aspartic acid). Surface modified nanofibers can be used alone or in combination with untreated nanofibers to form the nanofibrous polymer scaffold used in the engineered tissues or methods of making cartilage provided herein.

In other aspects, suitable nanofibrous polymer scaffolds include those manufactured from biodegradable polymers which degrade in vivo or in vitro, at a sufficiently slow rate to retain the desired nanoscale morphology during the tissue culturing process. In certain applications, the nanofibrous polymer scaffold is dimensionally stable for at least about 28 days, at least about 35 days, or at least about 42 days.

In certain embodiments, electrospinning of PCL-based nanofibers resulted in a scaffold composed of uniform, randomly oriented fibers of an average diameter of about 700 nm, as seen by scanning electron microscopy (FIG. 2A-B). Following an 8 week incubation in culture medium at 37° C., scaffolds maintained their integrity and three-dimensional structure, while exhibiting no noticeable change in dry weight over the entire culture period.

In certain embodiments, nanofibrous polymer scaffolds are composed of a biodegradable polymer which is dimensionally stable for at least the time period required to culture the cartilage or other tissue formed using the scaffold. FIG. 3A-F is a series of microscopic images of various nanofibrous scaffolds which are contemplated for use in the methods and cartilage provided herein. FIG. 4A-F provides a macroscopic observation of the degradation profile of various nanofibrous polymer scaffolds exposed to a phosphate buffered solution after 3, 7, 14, 21, and 42 days. After 42 days, substantial degradation occurred for nanofibrous scaffolds composed of PGA, PDLLA, PLGA 5050 and PLGA 8515. In contrast, nanofibrous scaffolds composed of PLLA and PCL retained their original structure after 42 days in the degradation medium.

FIG. 5A-F is a series of scanning electron microscope images of nanofibrous non-woven mats composed of PGA, PDLLA, PLLA, PLGA5050, PLGA8515, and PCL. Images are provided prior to exposure to a degradation medium (D0), after one day in the degradation medium (D1) and after three days in the degradation medium (D3). Nanofibrous scaffolds composed of PGA, PLLA and PCL retain the straight and uniform thickness nanofiber morphology after three days exposure to the degradation medium. PDLLA, PLGA5050, and PLGA8515 undergo substantial degradation including swelling, melting and other changes in nanofiber morphology.

The nanofibrous polymer support of the tissue engineered cartilage is composed of at least one biodegradable polyester. Certain preferred polymers include poly((L)-lactic acid), poly(epsilon-caprolactone) and blends thereof. In certain applications where additional tensile strength is required, non-biodegradable biocompatible nanofibers may be incorporated into the nanofibrous scaffold. In certain methods, including methods of preparing cartilage which typically take at least 28, 35, or 42 days, the nanofibrous polymer scaffolds are selected from those composed of PLLA, PCL, and blends thereof, optionally blended with one or more additional biodegradable or bioabsorbable polymers.

In yet other aspects, the nanofibrous polymer support comprises polymer nanofibers having a diameter of less than 1 micron or having a diameter of between 10 nm to 1 micron, 50 nm to 1 micron, 100 nm to 1 micron, or 200 nm to 500 nm.

Cells for Seeding onto the Nanofibrous Polymer Seafront

A variety of cells can be used to form engineered tissues. Chondrocytes, mesenchymal stem cells, and embryonic stem cells are generally preferred cells for the preparation of cartilage. Mesenchymal stem cells can be isolated from various tissues, including but not limited to muscle, blood, bone marrow, fat, cord blood, placenta, and other tissues known to contain mesenchymal stem cells.

Upon administration of chondrocytes to the nanofibrous polymer scaffold, the cells remain differentiated chondrocyte cells and begin to form extracellular matrix rich in collagen. Stem cells, including adult mesenchymal stem cells and embryonic stem cells, particularly MSC originating from a patient in need of replacement cartilage are suitable for use in the methods of the invention and differentiate to chondrocyte cells when the MSC cells are in contact with the nanofibrous polymer scaffolds used in the methods of the invention. Other collagen generating cells are also contemplated for use in the methods of the invention, including but not limited to tenocytes, ligamentum cells, fibroblasts, and dermal fibroblasts.

In certain aspects, the cells seeded on the nanofibrous polymer scaffold are a mixture of chondrocytes, mesenchymal stem cells, and/or embryonic stem cells and at least one other cell line which are beneficial for cartilage growth. In certain other aspects, the cells seeded on the nanofibrous polymer scaffold are a mixture of cells selected from chondrocytes, mesenchymal stem cells, and/or embryonic stem cells which are admixed with a biocompatible material. Biocompatible materials which are contemplated for admixing with cells in the preparation of engineered cartilage include biodegradable and non-biodegradable polymers and inorganic materials (such as ceramics and metals) which can be present as a fiber, nanoparticles, microparticle or mixture thereof. In certain aspects, these materials including nanofibers, cells, and other materials and agents are dispersed in the mixture of cells-nanofibers or structured in an organized way such as the layer-by-layer deposition.

In certain aspects where the engineered tissue is intended for implantation into a patient as part of a therapeutic, preventative, or cosmetic surgical procedure, autologous cells obtained by a biopsy are used as seed cells in the methods of engineering tissues or methods of engineering cartilage provided herein. Cells can be obtained directly from a donor, washed and suspended in a culture media before contacting the cells with the nanofibrous polymer support. To enhance cell viability, the cells are generally added or mixed with the culture media just prior to incorporation into the nanofibrous polymer scaffold.

Cell viability can be assessed using standard techniques including visual observation with a light or scanning electron microscope, histology, or quantitative assessment with radioisotopes. The biological function of the cells incorporated into the nanofibrous polymer scaffold can be determined using a combination of the above techniques.

Cells obtained by biopsy are harvested, cultured, and then passaged as necessary to remove non-cellular contaminants and contaminating, unwanted cells. Chondrocytes are isolated from autologous cartilage by excision of tissue, then either enzymatic digestion of cells to yield dissociated cells or mincing of tissue to form explants which are grown in cell culture to yield cells for seeding onto the nanofibrous polymer supports. Mesenchymal stem cells are isolated from autologous bone marrow. Typically bone marrow is harvested from the interior of the femoral neck and head by using a bone curet and then isolated from particulates and other cells (e.g., non-adherent hematopoietic and red blood cells) by centrifugation and exchange of culture medium.

Contacting the Cells and the Nanofibrous Polymer Substrate

In certain methods, a nanofibrous polymer non-woven mat is electrospun to a desired thickness and then cut to a desired shape to form the nanofibrous polymer scaffold. In certain embodiments, a solution of cells is then applied to at least a portion of the nanofibrous polymer substrate to form a cell-polymer matrix. During culturing the cells diffuse through the thickness of the nanofibrous polymer scaffold to form a cell-polymer matrix. In certain embodiments, the cells are selected from chondrocytes, mesenchymal stem cells, or embryonic stem cells or the cells are selected from chondrocytes and mesenchymal stem cells.

In certain instances, a cell culture tube is charged with the nanofibrous polymer substrate and then a solution of cells is added to the cell culture tube. The cell-substrate aggregate is then cultured statically in the tube to generate cartilage. As used herein, "statically cultured," "cultured in a static environment," or like terms are intended to refer to culturing conditions in which the culture medium is not moving relative to the cell-polymer matrix. In certain embodiments, the culture medium is a chondrogenic medium preferably comprising one or more growth factors. The static culturing is conducted at 37° C. in a humidified 5% carbon dioxide atmosphere. In certain methods comprising static culturing, the culture vessel is a conical cell culture tube, a culture medium and the cell-substrate aggregate are charged in the cell culture tube, and the mixture maintained at 37° C. under a humidified 5% carbon dioxide atmosphere. Culturing using a culture tube is referred to herein as "static" culturing.

In other methods, a nanofibrous polymer non-woven mat is expanded to introduce more porosity in the nanofibrous polymer scaffold. That is, in certain embodiments, an electrospun polymer mat is plucked, combed, teased or otherwise mechanically treated to increase the inter-fiber distances in the mat such that the expanded nanofibrous polymer scaffold has a "cotton ball" or fluffy appearance. The expanded mat is then contacted with a solution of cells. Although not wishing to be bound by theory, the increased inter-fiber distances present in the expanded nanofibrous polymer scaffold permits creates more apertures through which the cells can disperse into the expanded nanofibrous polymer scaffold thereby providing a more uniform distribution of cells throughout the scaffold after compression.

In certain methods, after combining the expanded nanofibrous polymer scaffold and the cell solution for between about 1 minute and about 8 hours, between about 5 minutes and about 6 hours, or between about 10 minutes and about 4 hours, the cell-scaffold aggregate is compressed. In general, any force capable of uniformly compressing the mixture of the nanofibrous polymer scaffold and the dispersed cells without causing undue damage to the viability of the cells is contemplated for use in the methods of the invention. In certain embodiments, the expanded nanofibrous polymer support is compressed by mechanical mans, e.g., by compressing between two or more impermeable objects such as a vessel wall and a non-porous rod or other implement. In certain other embodiments, application of centripetal force is used as a compression means. For example, a solution of the expanded nanofibrous polymer scaffold and dispersed cells is centrifuged for between 1 and about 10 minutes at between about 250 g and about 2500 g, or for between 2 and about 8 minutes at between about 500 g and about 2000 g to form a compressed cell-polymer matrix. Application of a compressive force compacts the expanded nanofibrous polymer scaffold entrapping the cells in the pores thereof. The substrate-solution mixture is then incubated in a chondrogenic medium for 1 hour to about 1 week under static conditions to permit the cell-polymer matrix to integrate.

In certain aspects, a compacted polymer-cell matrix is obtained by compressing the cell and expanded nanofibrous polymer scaffold mixture. For example, the cell and expanded nanofibrous polymer scaffold solution can be centrifuged at between about 250 g and about 2500 g to the polymer-cell matrix for 1 to 10 minutes. After centrifugation, the compacted polymer-cell matrix takes on the three dimensional shape of the bottom of the vessel in which the solution was centrifuged. That is, the bottom of the centrifugation vessel functions as a mold for the shape of the polymer-cell matrix formed during the centrifugation. Thus, for example, use of a centrifugation vessel having a bottom in the shape of an ear will result in an ear shaped polymer-cell matrix.

In certain embodiments, after centrifugation, the polymer-cell matrix is cultured for between 1 and about 10 days in a static environment to generate increased integration of the polymer-cell matrix. In certain other embodiments the polymer-cell matrix is cultured in a static vessel for between 2 to 10 days or between 3 and 7 days. Although not wishing to be bound by theory, the static culturing period is believed to allow the cells to generate an extracellular matrix which holds the fibers of the nanofibrous polymer support in position.

In certain aspects, after compression and static culturing, the polymer-cell matrix is transferred to a bioreactor for additional culturing of up to about 42 days during which time cartilage is formed. The term "bioreactor" is intended to refer to vessels suitable for culturing cells or cell-polymer matrixes, wherein the bioreactor improves delivery of nutrients and removal of waste products associated with cellular maintenance and development. Preferred bioreactor devices and vessels in which one or more biological or biochemical processes can be conducted under closely monitored and controlled conditions, e.g., environmental and/or operating conditions can be regulated by an operator. Certain bioreactors are devices in which the temperature, acidity (pH), pressure, nutrient supply, atmosphere, and/or removal of waste can be regulated by an operator or a control device. Bioreactors suitable for use in the methods of making tissue engineered cartilage provide a dynamic growth environment. The terms "dynamic," "cultured in a dynamic environment" and the like are intended to refer to culturing conditions in which the culture medium experiences at least one translational, rotational, or other mechanical force capable of causing the culture medium to flow or otherwise be translated in the bioreactor culture chamber. In general, bioreactors which generate movement of the culture medium relative to the cell-polymer matrix or the tissue engineered cartilage present in the bioreactor chamber are preferred.

In certain aspects, the bioreactor is selected from devices which direct a continuous flow of a culture medium or other fluid at the cell-polymer aggregate or tissue charged into the bioreactor culture chamber. In certain embodiments, the bioreactor is selected from spinner-flask bioreactors, rotating-wall vessel bioreactors, hollow fiber bioreactors, direct perfusion bioreactors, bioreactors that apply a controlled direct mechanical force to the cell-polymer aggregate or tissue, and other bioreactor designs that deliver continuous fluid flow to the cell-polymer aggregate or tissue. In certain other aspects, the bioreactor is a rotating bioreactor having a taurus shaped chamber charged with the cell-substrate aggregate and culture medium. The bioreactor is rotated about the central axis of the taurus at a rate sufficient to offset the force of gravity. In certain aspects, the use of a rotating bioreactor provides mechanical stresses such as compressive or shear stresses which contribute to the regulation of chondocytes in cartilage. Culturing using a rotating bioreactor such as a rotating bioreactor is referred to herein as "dynamic" culturing.

Figure 14:
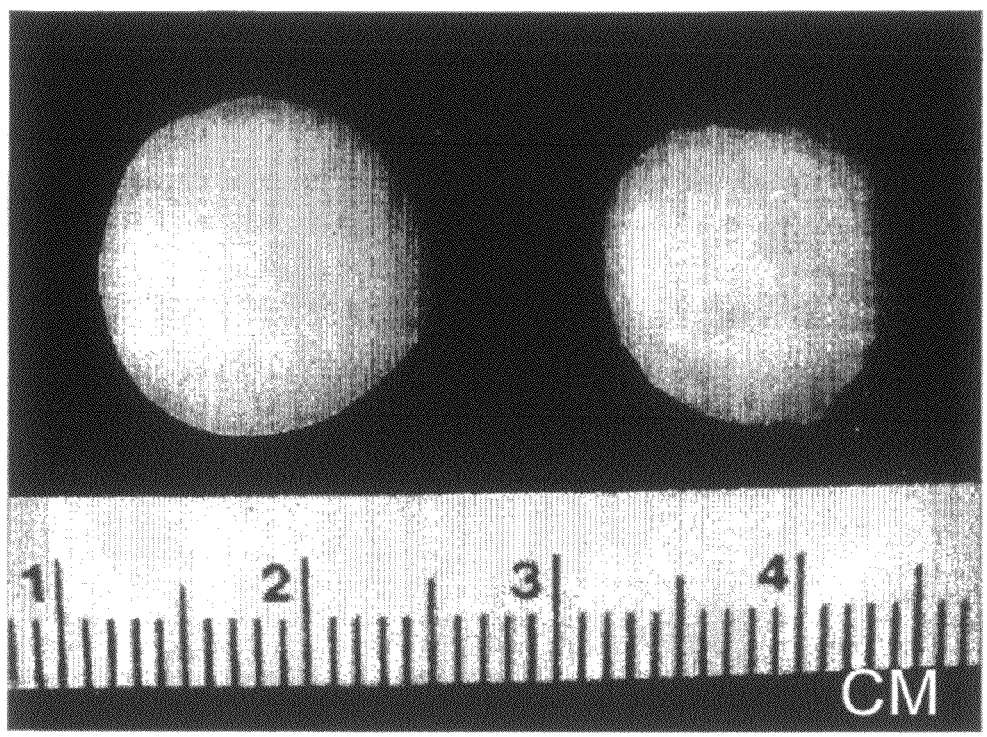
FIG. 14 is a photographic image comparing tissue engineered cartilage prepared by the dynamic method recited in Example 4 and tissue engineered cartilage prepared by a static method equivalent to the method of Example 4.
Figure 15:
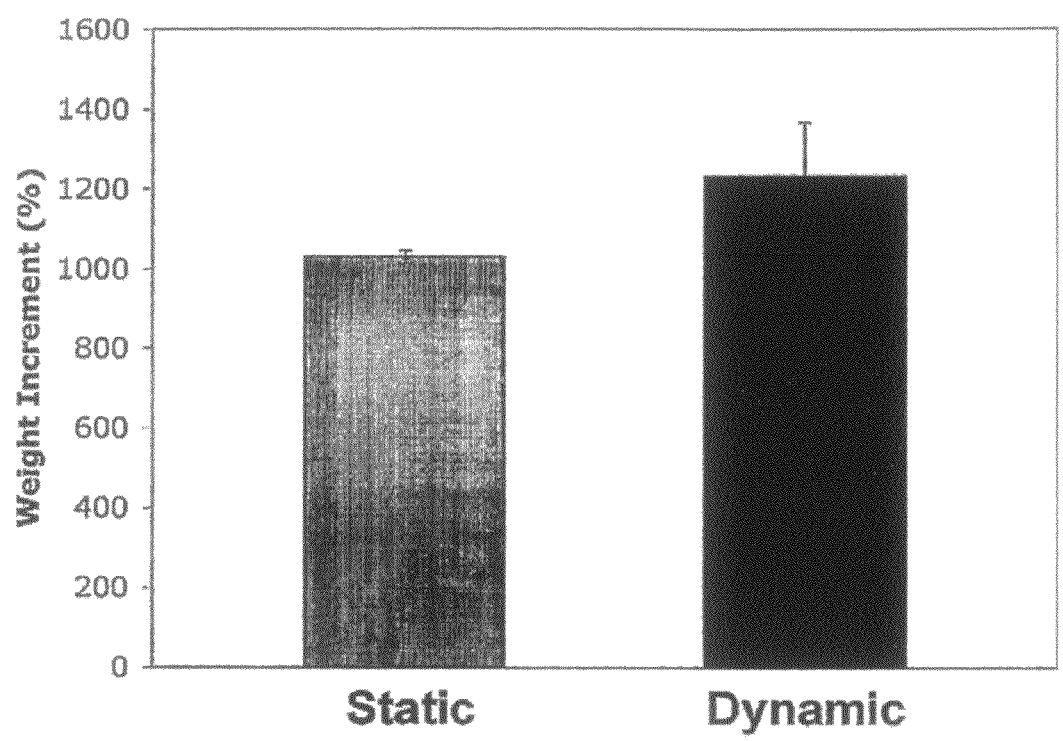
FIG. 15 is a bar graph comparing weight increase for tissue engineered cartilage prepared by the dynamic method recited in Example 4 (1200% increase) and tissue engineered cartilage prepared by a static method equivalent to the method of Example 4 (1000% increase)
Figure 16:
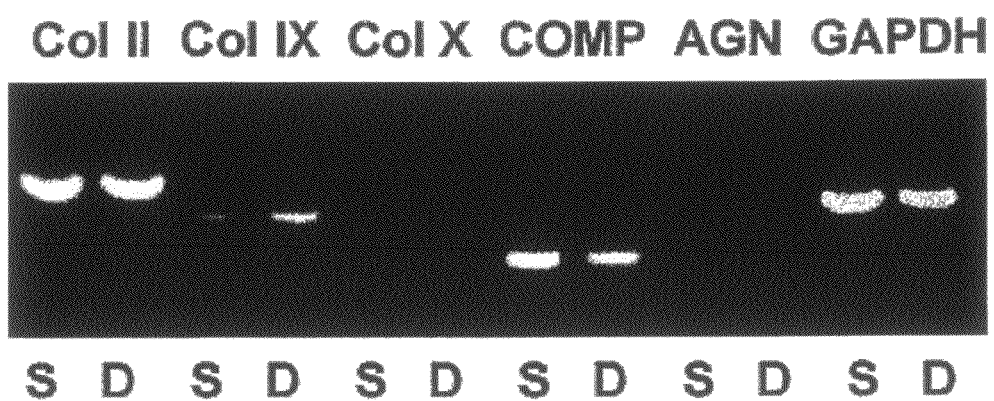
FIG. 16 is a series of images corresponding to RT-PCR analysis of cartilage prepared by the method of Example 4 under dynamic conditions and static conditions.
Figure 17:
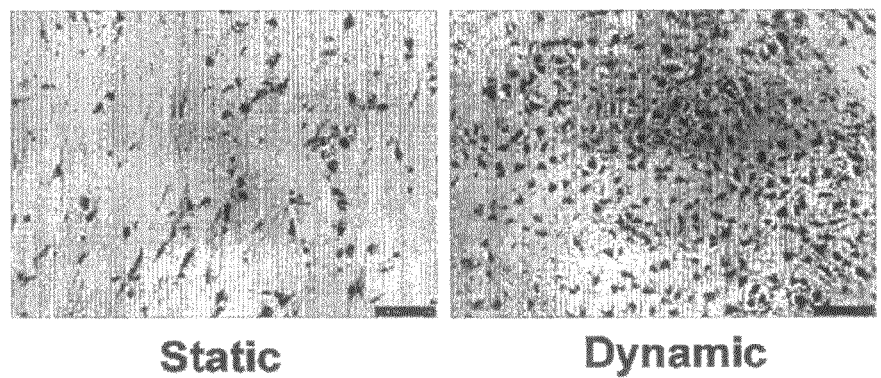
FIG. 17 is a series of photographs of the H & E staining histological analysis of cartilage prepared by the method of Example 4 under dynamic conditions and static conditions.
Figure 18:
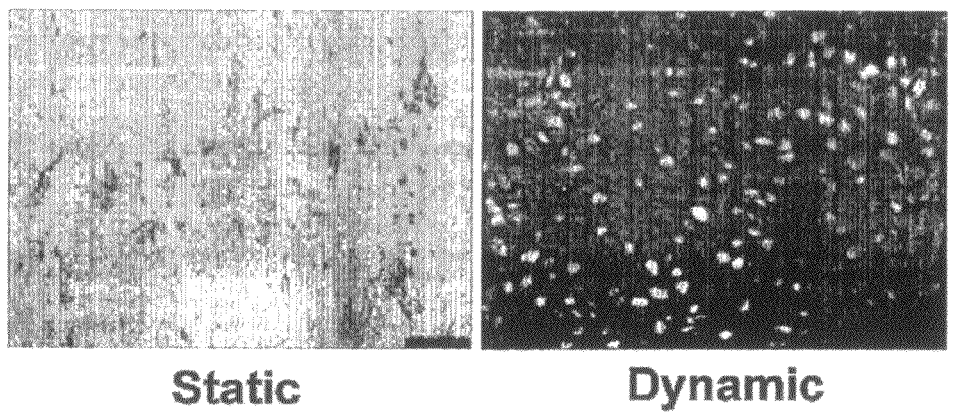
FIG. 18 is a series of photographs of the Alcian Blue histological analysis of cartilage prepared by the method of Example 4 under dynamic conditions and static conditions.
Figure 19:
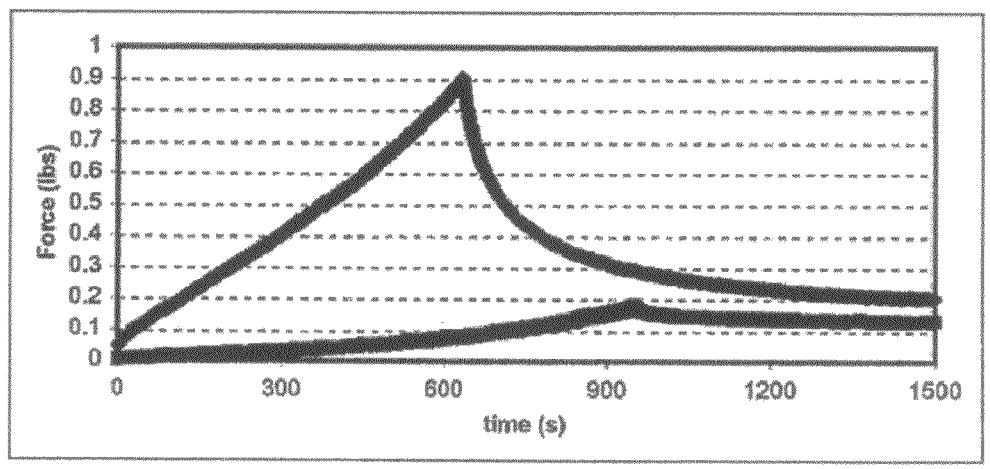
FIG. 19 is a graph of a compressive test for cartilage prepared by the method of Example 4 under dynamic conditions and static conditions.
Figure 20:
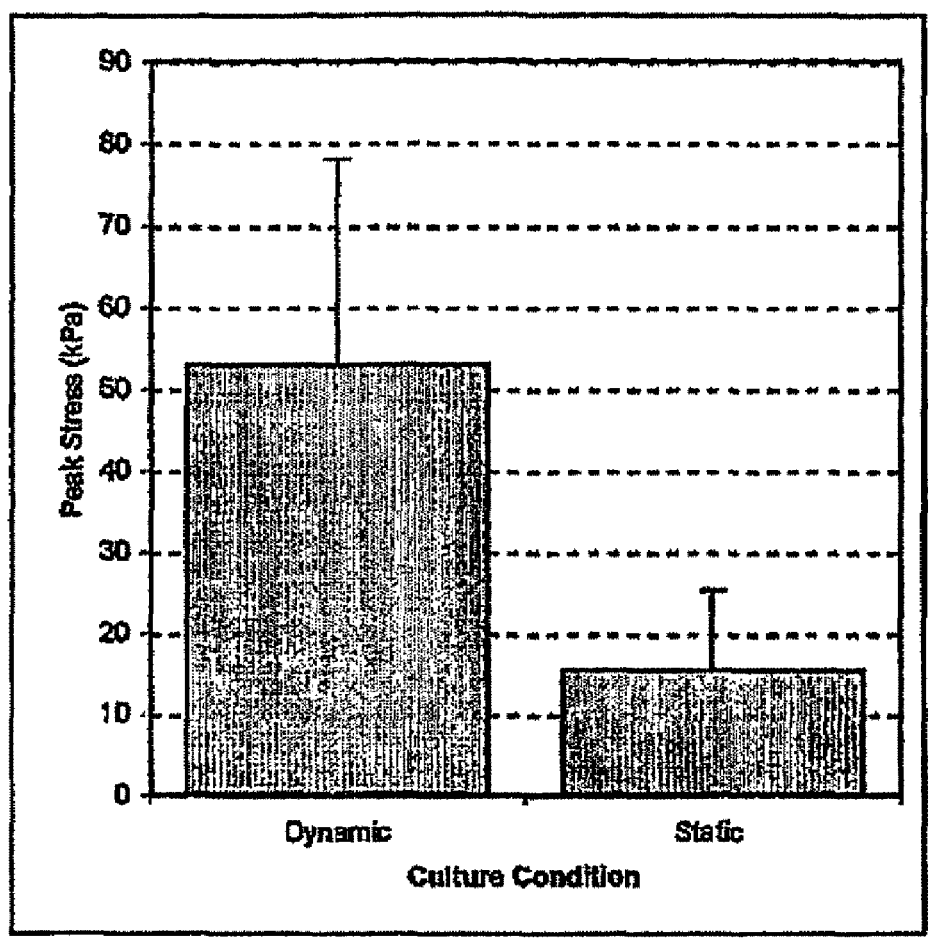
FIG. 20 is a bar graph of calculated stress for cartilage prepared by the method of Example under dynamic conditions and static conditions under dynamic conditions and static conditions under dynamic conditions and static conditions.

In certain aspects, tissue engineered cartilage prepared by dynamic culturing possesses mechanical and biochemical profiles which more closely mimic natural cartilage than tissue engineered cartilage prepared using a static culturing process. In FIG. 14 is a photographic comparison of tissue engineered cartilage prepared by the dynamic method recited in Example 4 and tissue engineered cartilage prepared by a static method equivalent to the method of Example 4. The dynamically cultured cartilage possesses a smoother glossier surface than the cartilage prepared using static culturing. Moreover, the weight gain observed for tissue engineered cartilage prepared using a dynamic culturing process is greater than cartilage prepared using a static culture for the same culturing period (see, FIG. 15). A histological and RT-PCR analysis comparison of cartilage prepared under dynamic and static culturing conditions are provided in FIG. 16-18. The mechanical properties (i.e., Young's modulus (FIG. 20) and compressive test (FIG. 19)) of dynamically cultured and statically cultured tissue engineered cartilage indicate that the dynamically cultured sample has greater strength under compression than statically cultured samples. Moreover, the dynamically cultured tissue engineered cartilage possesses a compressive strength and Young's modulus which is comparable to healthy native cartilage, e.g., a Young's modulus of between about 500 and about 800 MPa.

In certain aspects the culture medium is formulated to support the target engineered tissue. Thus, where cartilage is the target tissue, the culture medium is a chemically defined chondrogenic medium appropriate for maintenance of chondrocyte cells or inducing differentiation of mesenchymal stem cells to chondrocytes. In certain aspects, chemically defined chondrogenic media for use in the methods provided herein are substantially serum-free. Certain chemically defined chondrogenic media comprise one or more growth factors which regulate and/or promote chondrocyte formation, development or growth.

In certain methods provided herein, the culture medium comprises one or more growth factors suitable for promoting growth and development of chondrocytes and the differentiation of stem cells in to chondrocytes. In certain aspects, the growth factors are selected from transforming growth factors (TGF), insulin-lice growth factors (IGF), bone morphogenic proteins (BMP), fibroblast growth factors (FGF), and combinations thereof. In certain methods, the growth factors are selected from IGF-1, TGF-β1, TGF-β3, BMP-7 and combinations thereof. Thus, for example, culture medium comprising a mixture of TGF-β1 and IGF-1 provided cartilage having particularly desirable physical and biological properties, including increased Young's modulus.

Product Cartilage

One aspect is a tissue engineered cartilage having a peak compressive stress (Young's modulus) of greater than 250 MPa, which tissue engineered cartilage is composed of a plurality of chondocytes dispersed in a nanofibrous polymer support comprising a plurality of polymer nanofibers. In other aspects, the each of the plurality of chondocytes is in contact with at least one, at least two, or at a plurality of other chondocytes dispersed in the polymer support. In certain tissue engineered cartilages provided herein possess a peak compressive strength of at least about 300 MPa, about 400 MPa or about 500 MPa or a compressive strength of between about 250-1000 MPa, between about 300-1000 MPa, between about 300-900 MPa, or between about 400-900 MPa.

Certain tissue engineered cartilages provided herein are prepared by the cartilage tissue engineering methods depicted schematically in FIG. 6 and described in Example 4. The tissue engineered cartilage provided herein possess mechanical and biochemical properties analogous to natural cartilage, including but not limited to high Young's modulus of about 600-1000 Mpa, incorporation of lacunae in the cartilage morphology, elevated expression of cartilage specific proteins, and the like.

In certain embodiments, tissue engineered cartilage prepared by the methods of the invention possess lacunae (the voids present near chondrocytes in cartilage) and an extracellular matrix which resembles that of natural cartilage. Certain methods produce cartilage which has a peak compressive strength equivalent to natural cartilage and possess lacunae, the empty space surrounding chondocytes in healthy cartilage, which is similar to natural cartilage.

A series of tissue engineered cartilages were prepared by the method recited in Example 4, in which the growth factors added to the culture medium was varied from no growth factors (control), TGF-β1 alone, IGF-1 alone, or a combination of TGF-β1 and IGF-1. The resultant cartilage were analyzed using several biochemical and mechanical tests.

Figure 7:
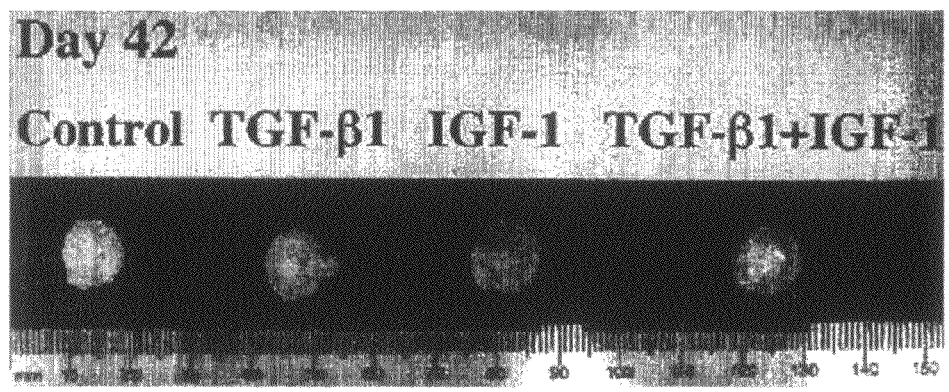
FIG. 7 is a picture of the tissue engineered cartilage prepared in Example 4 cultured in the chondrogenic medium supplemented with different growth factors after 42 days (Control had no Growth Factors)
Figure 8:
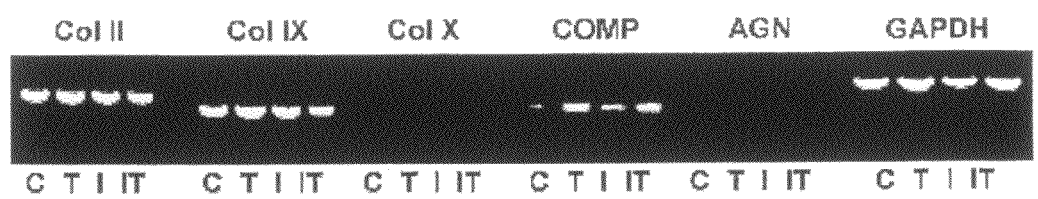
FIG. 8 is a series of images corresponding to RT-PCR analysis of cartilage prepared by the method of Example 4 with different growth factors (control, TGF-β1, IGF-1, and TGF-β1+IGF-1)
Figure 9:
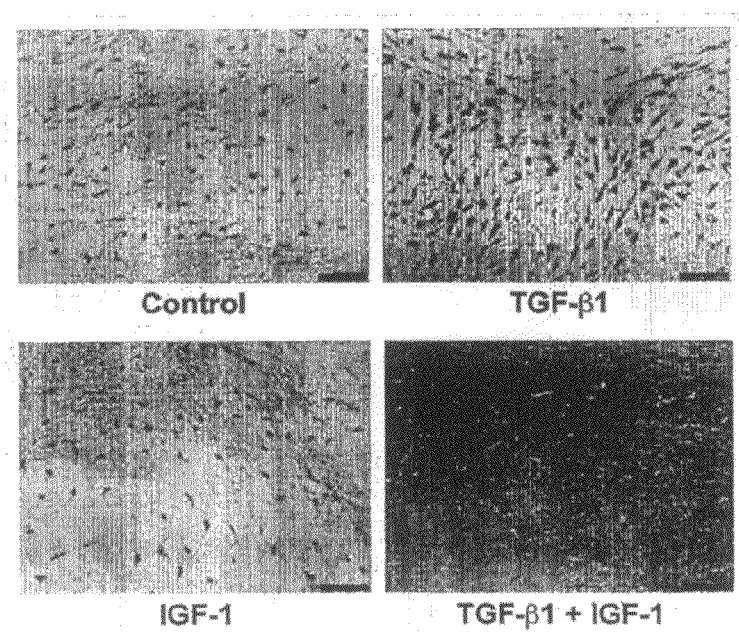
FIG. 9 is a series of photographs of the H & E staining histological analysis of cartilage prepared by the method of Example 4 with Different Growth Factors (control, TGF-β1, IGF-1, and TGF-β1+IGF-1)
Figure 10:
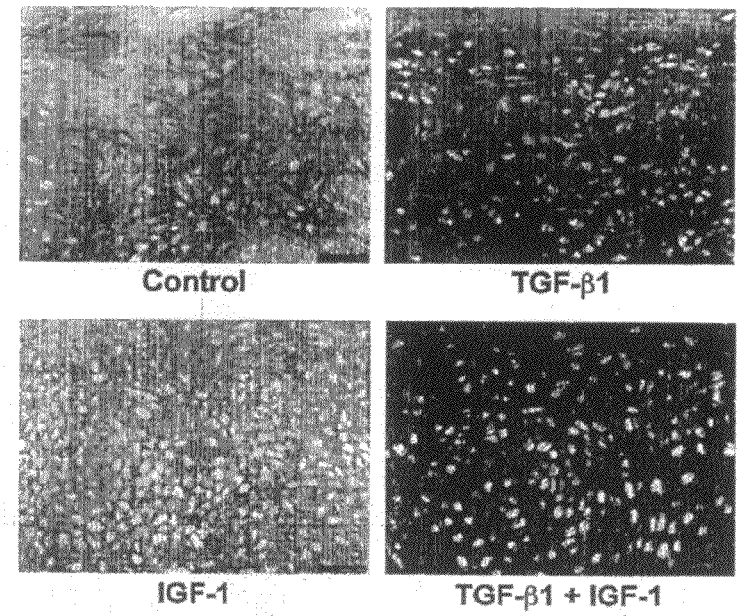
FIG. 10 is a series of photographs of the Alcian Blue histological analysis of cartilage prepared by the method of Example 4 with different growth factors (control, TGF-β1, IGF-1, and TGF-β11+IGF-1)
Figures 11A, 11B:
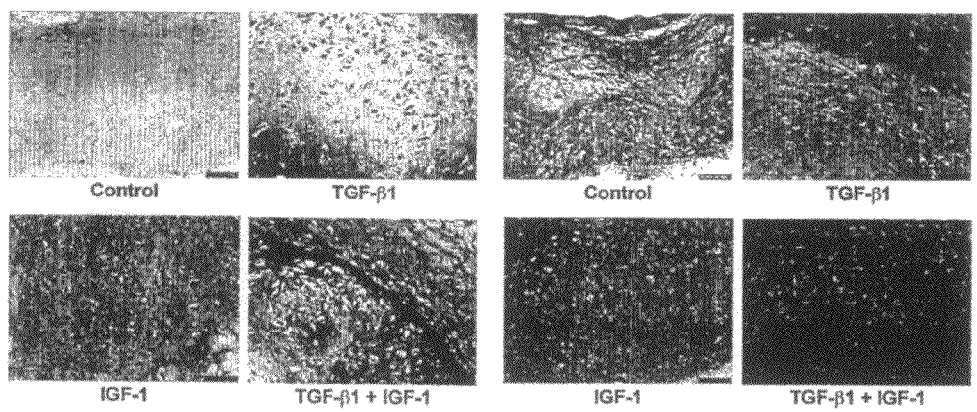
FIG. 11 is a series of photographs showing the immunohistochemical localization of cartilage-specific ECM in cartilage prepared by the method of Example 4 with Different Growth Factors (control, TGF-β1, IGF-1, and TGF-β1+IGF-1)

FIG. 6 is a tissue engineered flow chart of one of the methods of preparing tissue engineered cartilage provided herein and exemplified in Example 4;

FIG. 7 is a picture of the tissue engineered cartilage prepared in Example 4 cultured in the chondrogenic medium supplemented with different growth factors after 42 days (Control had no growth factors) FIG. 8 is a series of images showing expression of cartilage specific proteins by RT-PCR analysis in the cells of the tissue engineered cartilage prepared in Example 4 cultured in the chondrogenic medium supplemented with different growth factors after 42 days (control, TGF-β1, IGF-1, and TGF-β1+IGF-1). Histological analysis of cartilage prepared in Example 4 cultured in a chondrogenic medium supplemented with different growth factors after 42 days is provided by the images of FIG. 9 and FIG. 10. More particularly, FIG. 9 provides a series of photographs of tissue engineered cartilage samples with H&E staining. FIG. 10 provides a series of photographs of tissue engineered cartilage samples with Alcian blue staining. FIG. 11 is a series of photographs showing the immunohistochemical localization of cartilage-specific ECM in the tissue engineered cartilage prepared by the method of Example 4 The histology indicates that the tissue samples possess a cartilage like extracellular matrix and chondrocytes dispersed in the tissue. FIG. 11 is a series of photographs showing the immunohistochemical localization of cartilage-specific ECM in cartilage prepared by the method of Example 4 cultured in a chondrogenic medium supplemented with different growth factors after 42 days.

Figure 12:
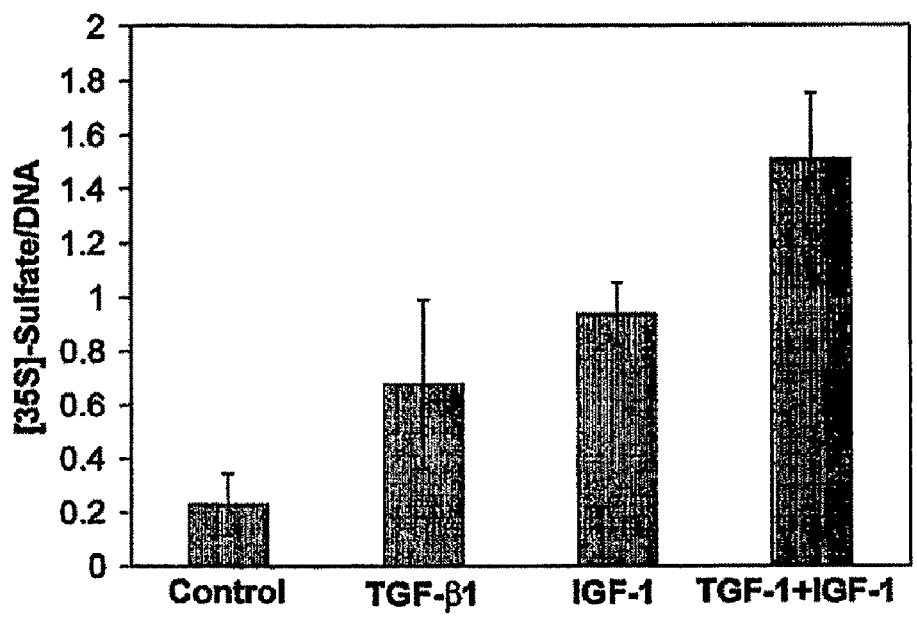
FIG. 12 is a bar graph of radioactive sulfate incorporation in cartilage prepared by the method of Example 4 with different growth factors (control, TGF-β1, IGF-1, and TGF-β1+IGF-1)
Figure 13:
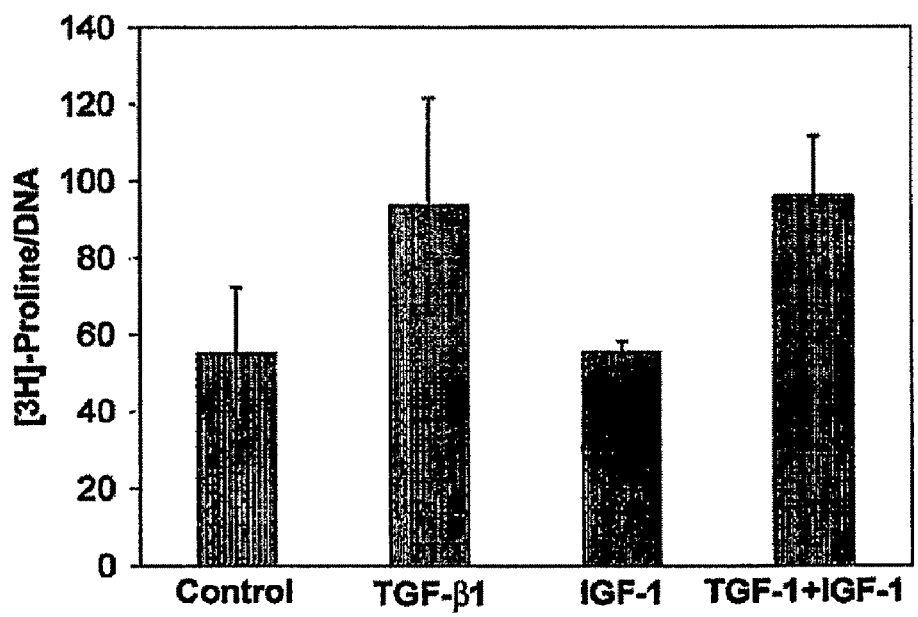
FIG. 13 is a bar graph of radioactive proline incorporation in cartilage prepared by the method of Example 4 with different growth factors (control, TGF-β1, IGF-1, and TGF-β1+IGF-1)

Uptake of radiolabeled sulfate and radiolabeled proline by the tissue engineered cartilage indicates chondrocyte activity and development of cartilage specific ECM in the tissue engineered cartilage. FIG. 12 is a bar graph of radioactive sulfate incorporation in cartilage prepared by the method of Example 4 with different growth factors (control, TGF-β1, IGF-1, and TGFβ1+IGF-1). FIG. 13 is a bar graph of radioactive proline incorporation in cartilage prepared by the method of Example 4 with different growth factors (control, TGF-β1, IGF-1, and TGF-β11+IGF-1).

In certain aspects, the tissue engineered cartilage provided herein are compatible with natural cartilage. Thus, for example, natural cartilage grafted to a tissue engineered cartilage prepared by the methods of the invention integrate when cultured in vitro such that after culturing for several weeks the interface between natural and tissue engineered cartilage fades.

In-vivo Cartilage Formation

Another aspect is a method of forming cartilage in vivo, the method comprising the steps of (a) providing a nanofibrous polymer support comprising a plurality of polymer nanofibers; and (b) inserting the nanofibrous polymer support into a patient at the position suitable for formation of new cartilage.

In certain aspects, the nanofibrous polymer scaffolds suitable for use in the in vitro methods of preparing cartilage are also suitable for implantation into a patient at situs in need of new cartilage. Suitable nanofibrous polymer scaffolds for incorporation into a patient include PCL and PLLA and further include other biodegradable polyesters which provide a dimensionally stable scaffold for chondrocyte development in the area requiring new cartilage. Thus, for example, PGA which is morphologically stable under SEM analysis after three days (FIG. 3), but degrades rapidly between day 21 and day 42 (FIG. 4 and FIG. 5) is also contemplated for use as a nanofibrous polymer support in the in vivo cartilage formation methods of the invention.

In certain aspects, the methods of making cartilage are suitable for producing elastic cartilage, fibrocartilage, or hyaline cartilage depending upon the cell type used, the method selected, the growth factors added to the culture medium, the composition of the support scaffold and the presence or absence of additional materials in the support structure, such as ceramics, bone mimetics, high tensile strength bio-compatible fibers and the like. Cartilage is a specialized type of dense connective tissue consisting of cells embedded in a matrix. There are several kinds of cartilage. Hyaline cartilage is a bluish-white, glassy translucent cartilage having a homogeneous matrix containing collagenous fibers which is found in articular cartilage, in costal cartilages, in the septum of the nose, and in the larynx and trachea. Articular cartilage is hyaline cartilage covering the articular surfaces of bones. Costal cartilage connects the true ribs and the sternum. Fibrocartilage is a connective tissue primarily located in intervertebral disc. Elastic cartilage is primarily in the epiglottis, the external ear, and the auditory tube. By harvesting the appropriate chondrocyte precursor cells, any of these types of cartilage tissue can be grown using the methods of the invention.

Methods of Tissue Engineering

The tissue engineering methods described supra are directed to the preparation of tissue engineered cartilage, the methods are equally suited to the preparation of other tissue engineered or engineered tissues. Thus, for example, substituting cells obtained from other tissues for chondrocytes, or replacing the chondrogenic medium with media suited for other tissues in the methods of tissue engineering and methods of preparing cartilage recited supra, will generate other tissues.

Certain methods of engineering tissue are suitable for use in forming bone, muscle, tendon, ligaments, and other tissues. Thus, the methods of cartilage formation provided herein are modified by (a) contacting the nanofibrous polymer support with cells appropriate for the desired tissue, and (b) adding tissue appropriate growth factors to the culture medium. In certain aspects, including for example, methods of making tendon and/or ligament, the use of a non-biodegradable nanofibrous polymer support is desirable to provide additional tensile strength to the engineered tendon or ligament.

III. Methods of Treatment

In other aspects, the invention provides methods of repairing, replacing and/or augmenting cartilage in a patient for treatment or prevention of diseases or disorders or for cosmetic purposes. In certain aspects, a method of treating cartilage damage is provided in which the method comprising the steps of:

(a) providing a tissue engineered cartilage having a peak compressive stress (Young's modulus) of greater than 250 MPa, which tissue engineered cartilage is composed of a plurality of chondrocytes dispersed in a nanofibrous polymer support comprising a plurality of polymer nanofibers or a tissue engineered cartilage prepared by the methods provided herein;

(b) inserting the tissue engineered cartilage into a patient at the location of damaged cartilage.

Another aspect is a method for treating cartilage damage, the method comprising the steps of (a) harvesting chondrocytes or MSC cells from the patient;

(b) preparing tissue engineered cartilage by one of the methods provided herein, wherein the cells are the chondocytes or MSC cells harvested from the patient;

(c) implanting the tissue engineered cartilage in the patient in the locus having damaged cartilage.

Yet another aspect is a method for cosmetic or reconstructive surgery, the method comprising the steps of (a) providing a tissue engineered cartilage having a peak compressive stress (Young's modulus) of greater than 250 MPa, which tissue engineered cartilage is composed of a plurality of chondrocytes dispersed in a nanofibrous polymer support comprising a plurality of polymer nanofibers or a tissue engineered cartilage prepared by the methods provided herein;

(b) inserting the tissue engineered cartilage into a patient

In another aspect, the invention provides a method for cosmetic or reconstructive surgery, the method comprising the steps of (a) harvesting chondrocytes or MSC cells from the patient;

(b) preparing tissue engineered cartilage by a method provided herein, wherein the cells are the chondocytes or MSC cells harvested from the patient;

(c) implanting the tissue engineered cartilage in the patient.

In one embodiment, the present invention provides methods of treating disease and/or disorders or symptoms thereof which comprise administering a nanofibrous polymeric support, an engineered tissue or engineered cartilage provided herein to a subject (e.g., a mammal such as a human). More particularly, the present invention provides methods of treating damaged or destroyed cartilage by inserting tissue engineered cartilage herein at the locus of cartilage damage or destruction in the patient. Thus, for example, a patient suffering from arthritis of the knee may have damaged or destroyed some or all of the cartilage interposed between the femur, the fibula, and/or the patella. The methods of the invention provide for treatment by inserting tissue engineered cartilage or inserting a nanofibrous polymer support in the knee at the point of damage to replace or repair the damaged cartilage.

In certain other aspects, engineered cartilage provided herein is administered to a subject (e.g., a mammal such as a human) to provide desirable reconstructive or cosmetic benefit to the patient. Thus, for example, a patient sustained an injury which caused damage or destruction of the cartilage of the ear or nose. The methods of the invention provide for reconstruction or cosmetic enhancement of the ear or nose by inserting a formed engineered cartilage into the damaged nose or ear thereby improving the function or aesthetics of the nose or ear.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

As used "cosmetic surgery" or "reconstructive surgery" is intended herein to refer to surgical procedures intended to modify or improve the appearance of a physical feature, irregularity, or defect.

The invention will be further described in the following examples. It should be understood that these examples are for illustrative purposes only and are not to be construed as limiting this invention in any manner.

EXAMPLE 1

Isolation and Culture of Bone Marrow-derived hMSCs

With approval from the Institutional Review Board of Thomas Jefferson University, bone marrow-derived hMSCs were obtained from the femoral heads of patients undergoing total hip arthroplasty, and processed as previously described (Noth U, et al. J Orthop Res 2002;20:1060-9; Haynesworth S E, et al. Bone 1992;13:81-8; and Wang M L, et al. J Orthop Res 2002;20:1175-84). Briefly, whole bone marrow was curetted from the exposed cutting plane of the femoral neck, washed extensively in Dulbecco's Modified Eagle's medium (DMEM; BioWhittaker, Walkersville, Md.), separated from contaminating trabecular bone fragments and other tissues using a 20-gauge needle attached to a 10-cc syringe, and cultured in DMEM, 10% fetal bovine serum (FBS; Premium Select, Atlanta Biologicals, Atlanta, Ga.) from selected lots (Caterson E J, et al. Mol Biotechnol 2002;20:245-56), and antibiotics (50 µg/mL streptomycin, 50 IU/mL of penicillin; Cellgro, Herndon, Va.) at a density of $4\times10^5$ cells/cm$^2$. Six hours post-plating, tissue culture flasks were washed twice with phosphate-buffered saline (PBS) to remove non-adherent cells. Medium changes were made every 3-4 days. Subconfluent cell monolayers were dissociated using 0.25% trypsin (Gibco BRL, Life Technologies, Grand Island, N.Y.) and either passaged or utilized directly for study.

EXAMPLE 2

Fabrication of Electrospun Nanofibrous PCL Scaffolds

Nanofibrous scaffolds were fabricated according to an electrospinning process described previously (Li W J, et al. J Biomed Mater Res 2003;67A:1105-14). Briefly, PCL polymer was dissolved in an organic solvent mixture (1:1) of tetrahydrofuran (THF; Fisher, Pittsburgh, Pa.) and N,N, dimethylformamide (DMF; Fisher, Pittsburgh, Pa.) at a final concentration of 0.14 g/mL. The polymer solution was delivered through the electrospinning apparatus at a constant flow rate of 0.4 mL/h under an applied 0.6 kV/cm charge density, resulting in a 144 cm$^2$ mat with an approximate thickness of 1 mm. To remove residual organic solvent, the non-woven polymer mat was placed within a vacuum chamber for 48 h, and subsequently stored in a desiccator. Prior to cell seeding, squares measuring 10 mm×10 mm×1 mm were fashioned from the electrospun mat, sterilized by ultraviolet irradiation for 30 min per side in a laminar flow hood, and pre-wetted for 24 h in Hanks' Balanced Salt Solution (HBSS; BioSource International, Camarillo, Calif.).

EXAMPLE 3

Seeding and Differentiation of hMSCs on PCL Scaffolds

Pre-processed nanofibrous PCL scaffolds were placed in 24-well tissue culture plates (Corning Glass Works, Corning, N.Y.) coated with 0.3% poly(2-hydroxyethyl methacrylate) (poly HEMA; Polysciences, Warrington, Pa.) to prevent normal cell attachment to tissue culture polystyrene. Cellular scaffolds were incubated at 37° C. for 4 h to allow MSCs to diffuse into and adhere to the scaffold before the addition of 2 mL of culture medium to each well. During the 4 h incubation, 20 µL of serum containing culture medium was applied every 30 min to each cellular scaffold to prevent the constructs from drying. For chondrogenic differentiation studies, 4×10$^5$ hMSCs were seeded per PCL scaffold and maintained in a chemically defined medium containing serum-free DMEM, 50 µg/mL ascorbate, 0.1 µM dexamethasone, 40 µg/mL L-proline, 100 µg/mL sodium pyruvate, ITS-plus (Collaborative Biomedical Products, Cambridge, Mass.), antibiotics, and 10 ng/mL recombinant human transforming growth factor-β1 (TGF-β1; R&D Systems, Minneapolis, Minn.) (Johnstone B, et al. Exp Cell Res 1998;238:265-72; Yoo J U, et al. J Bone J Surg Am 1998;80:1745-57; and Mackay A M, et al. Tissue Eng 1998;4:415-28). Control cell scaffolds were maintained without the addition of TGF-β1. For osteogenesis and adipogenesis, hMSCs were seeded at a density of 2×10$^5$ cells/scaffold. Osteogenic induction was accomplished using DMEM supplemented with 10% FBS, 50 µg/mL ascorbate, 10 mM β-glycerophosphate, 0.1 µM dexamethasone, and antibiotics (Pittenger M F, et al. Science 1999;284:143-7). Finally, adipogenesis was induced using DMEM supplemented with 10% FBS, 1 µM dexamethasone, 0.5 mM 3-isobutyl-1-methylxanthine, 1 µg/mL insulin, and antibiotics (Pittenger M F, et al. Science 1999;284:143-7). Control cultures were maintained without osteogenic and adipogenic supplements, respectively. All cell scaffolds were maintained for 21 days in a humidified incubator at 37° C. and 5% CO2 with medium changes every 3-4 days.

EXAMPLE 4

Preparation of Tissue Engineered Cartilage Using Dynamic Culturing 4.1. Electrospin Nanofibers 1.6 gm of tissue engineered, biodegradable PLLA is dissolved in 10 mL of chloroform and 2 mL of DMF for overnight. The PLLA polymer solution is placed in a 10 mL syringe with a metal needle and the tip of needle is 10 cm away from the collecting plate. 16 kV of voltage is applied to the polymer solution. After 8 hour of electrospinning, 12×12 cm of nanofibrous mat is produced.

4.2. Expand the Nanofibers to Form an Expanded Nanofibrous Polymer Support

Use two metal specula to manually loosen and fluff nanofibers. Weigh 30 mg of fluffy nanofibers and place it in a 50 mL tissue culture conical tube. 20 mL of 100% of ethanol is added in the tube and shake the tube to further separate and disperse individual nanofibers in the ethanol suspension. Replace the ethanol liquid phase with a balanced salt solution by a gradient fluid exchange, e.g., exchange the 100% ethanol with 70% ethanol, then with 30% ethanol, then with 100% pure water, and then finally with balanced salt solution.

4.3. Combine Cells and Fluffy Nanofibers

Chondrocytes grown on a monolayer culture is trypisnized and 10 million of cells in 1 mL of 10% FBS containing medium is placed in a nanofiber containing tube. Cells and nanofibers are well mixed by gently shaking the tube. The cell-nanofiber mixture is left in an incubator for 1.5 hour, packed tightly using a long bar with a flat surface at the end, and centrifuged at the speed of 1500 g for 5 min. The cell-nanofiber aggregation is cultured in the 50 mL conical tube for additional 7 days before it is removed to a dynamic culture system.

4.4. Culture Cell-Polymer Aggregate in a Rotating Vessel Wall Bioreactor

The cell-nanofiber composite is placed in a rotating vessel wall bioreactor for next 42 days. The rotation speed of a rotating-wall vessel bioreactor is controlled to maintain the cell-nanofiber composite stay in the situation of floating in the medium. The cell-nanofiber composite is cultured in the chondrogenic medium supplemented with 10 ng/mL of transforming growth factor-beta 1(TGF-1) and 50 ng/mL of insulin-like growth factor and half the volume of the cell culture medium is replaced every three days.

EXAMPLE 5

Physical and Biochemical Analysis Methods 5.1. Scanning Electron Microscopy (SEM)

For each condition, two cell-polymer constructs were fixed in 2.5% glutaraldehyde, dehydrated through a graded series of ethanol, vacuum dried, mounted onto aluminum stubs, and sputter coated with gold. Samples were examined using a scanning electron microscope (S-4500; Hitachi, Japan) at an accelerating voltage of 20 kV.

5.2. Reverse Transcription Polymerase Chain Reaction (RT-PCR) Analysis

Total cellular RNA was extracted using Trizol Reagent (Gibco BRL, Life Technologies, Grand Island, N.Y.) according to the manufacturer's protocol. For efficient yield, six cell-scaffolds from the same culture condition were first briefly homogenized in Trizol Reagent using a pestle (Kontes, Vineland, N.J.). Concentrations of RNA samples were estimated on the basis of OD$_{260}$. RNA samples were reverse transcribed using random hexamers and the SuperScript First Strand Synthesis System (Gibco BRL, Life Technologies, Grand Island, N.Y.). PCR amplification of cDNA was carried out using AmpliTaq DNA Polymerase (Perkin Elmer; Norwalk, Conn.) and the gene-specific primer sets listed in Table 1 of Li, et al., *Multilineage Differentiation of human mesenchymal stein cells in three-dimensional nanofibrous scaffold*, Biomaterials, 2005. These genes included adipose specific genes-, lipoprotein lipase (LPL) and peroxisome proliferatoractivator receptor-γ2 (PPAR γ2); cartilage specific genes-, aggrecan (AGN), collagen type II (Col II), and collagen type X (Col X); and bone specific genes-, alkaline phosphatase (ALP), bone sialoprotein (BSP), collagen type Iα2 (Col Iα2), and osteocalcin (OC). Thirty-two cycles were used for all genes, and consisted of 1-min denaturation at 95° C., 1-min annealing at 57° C. (AGN, Col II, and Col X) or 51° C. (all remaining genes), 1-min polymerization at 72° C., followed by a final 10-minute extension at 72° C. The housekeeping gene, glyceraldehyde 3-phosphate dehydrogenase (GAPDH), was used as a control for RNA loading of samples. PCR products were analyzed electrophoretically using the Agilent 2100 Bioanalyzer (Agilent Technologies, Palo Alto, Calif.).

5.3. Cryoembedding and Sectioning

For each condition, two of each adipogenic, chondrogenic, and osteogenic cellular constructs were harvested following 21 days of culture, fixed in 4% PBS-buffered paraformaldehyde for 15 min, washed three times with PBS, infiltrated with 20% sucrose, embedded with Tissue-Tek O.C.T Compound (Sakura Finetek USA, Inc., Torrance, Calif.), and cryo-sectioned at 8 mm thickness using the Leica CM 1850 (Bannockburn, Ill.) cryostat microtome.

5.4. Histological Analysis

Control and adipogenic cell-polymer constructs were incubated in 60% isopropanol for 5 min, followed by Oil Red O stain for 5 min. The cells were then rinsed with tap H2O and counterstained with hematoxylin for 1 min. Cell-polymer constructs maintained in chondrogenic medium with or without TGF-β1(10 ng/mL) were stained with alcian blue (pH 1.0), as previously described (Denker A E, et al. Differentiation 1999;64:67-76). Control and osteogenic cell-polymer constructs were stained histochemically for alizarin red, as previously described (Puchtler H, et al. J Histochem Cytochem 1969;17:110-24), and alkaline phosphatase (Sigma Cat. No. 86-C) according to the manufacturer's protocol. Two samples from each condition were prepared for this analysis.

5.5. Immunohistochemical Analysis

Immunohistochemistry was used to detect aggrecan, collagen type II, and link protein, in control and treated chondrogenic cell-polymer constructs, and bone sialoprotein, and collagen type I in control and treated osteogenic cell-polymer constructs. Sections were pre-digested for 15 min at 37° C. in 1.5 U/mL of chondroitinase A/B/C before they were incubated for 1 h at 37° C. in 10 mg/mL of aggrecan primary antibody (1-C-6; Developmental Studies Hybridoma Bank, Iowa City, Iowa). Bone sialoprotein and collagen type I were detected using primary antibodies at a 1:500 dilution (BSP; Chemicon International, Temecula, Calif.) and 15 μg/mL (SP1.D8; Developmental Studies Hybridoma Bank), respectively, for 1 h at 37° C. Antigen—antibody complexes were detected colorimetrically using the Broad Spectrum Histostain-SP Kit (Zymed Laboratories, Inc., South San Francisco, Calif.); sections were counterstained with hematoxylin.

Incorporation by Reference

All patents, published patent applications, and other references disclosed herein are hereby expressly incorporated by reference in their entireties by reference.

Equivalents

Those skilled in the art will recognize, or be able to ascertain using no more than routine experimentation, many equivalents of the specific embodiments of the invention described herein. Such equivalents are intended to be encompassed by the following claims.

What is claimed is:

1. A tissue engineered cartilage, comprising
a nanofibrous polymer support comprising a plurality of polymer nanofibers; and
a plurality of chondrocytes dispersed throughout the polymer support, wherein the tissue engineered cartilage has a peak compressive stress (Young's modulus) of greater than 250 Mpa wherein the nanofibrous polymer support comprises a non-woven mat of electrospun nanofibers having a diameter of less than 1 micron, and wherein the nanofibers of the non-woven mat are randomly oriented.

2. The tissue engineered cartilage of claim 1, wherein the nanofibrous polymer support comprises polymer nanofibers having a diameter of less than 1 micron.

3. The tissue engineered cartilage of claim 2, wherein the polymer nanofibers have a diameter of between 50 nm and 1 micron.

4. The tissue engineered cartilage of claim 2, wherein the polymer nanofibers have a substantially uniform diameter.

5. The tissue engineered cartilage of claim 1, wherein the nanofibrous polymer support is composed of at least one biodegradable polyester or blend thereof.

* * * * *